(12) United States Patent
Glaister et al.

(10) Patent No.: US 10,213,356 B2
(45) Date of Patent: Feb. 26, 2019

(54) ORTHOSIS DEVICE

(71) Applicant: Cadence Biomedical, Seattle, WA (US)

(72) Inventors: Brian Glaister, Seattle, WA (US);
Jason Panzenbeck, Seattle, WA (US);
Jason Schoen, Seattle, WA (US); Chie Kawahara, Seattle, WA (US)

(73) Assignee: Cadence Biomedical, Seattle, WA (US)

( * ) Notice: Subject to any disclaimer, the term of this patent is extended or adjusted under 35 U.S.C. 154(b) by 405 days.

(21) Appl. No.: 14/965,769

(22) Filed: Dec. 10, 2015

(65) Prior Publication Data

US 2019/0015286 A1     Jan. 17, 2019

(51) Int. Cl.
*A61H 3/00*     (2006.01)
*A61F 2/60*     (2006.01)
*A61F 5/01*     (2006.01)

(52) U.S. Cl.
CPC .............. *A61H 3/00* (2013.01); *A61F 2/604* (2013.01); *A61F 5/0125* (2013.01); *A61F 2005/0134* (2013.01)

(58) Field of Classification Search
CPC ................. A61F 5/0123; A61F 5/0125; A61F 2005/0139; A61F 5/0102; A61F 2005/0167; A61F 2005/0134; A61F 5/0111; A61F 5/0585; A61F 5/0195; A61F 5/0127; A61H 3/00
See application file for complete search history.

*Primary Examiner* — Ophelia A Hawthorne
(74) *Attorney, Agent, or Firm* — FSP LLC

(57) ABSTRACT

An apparatus includes a harness, at least one brace that may include an articulated frame coupled to the harness, a pre-tensioning device, a lower assembly coupled to the articulated frame, and an energy-transforming mechanism that may be adjusted to a user and may assist with the user's gait. The energy-transforming mechanism may include an energy storage device coupled to the pre-tensioning device via a superior exotendon and coupled to the lower assembly via an inferior exotendon.

12 Claims, 7 Drawing Sheets

ORTHOSIS DEVICE

BACKGROUND

A medical apparatus is often used by a patient that has lost some functionality of one or both of their legs. An orthosis may be used to control, guide, limit and/or immobilize an extremity, joint or body segment for a particular reason; to restrict movement in a given direction; to assist movement generally; to reduce weight bearing forces for a particular purpose; to aid rehabilitation from fractures after the removal of a cast; and/or to otherwise correct the shape and/or function of the body to provide easier movement capability or reduce pain.

An obstacle in orthosis design is to provide the patient with a natural gait. The patient often needs assistance moving the limb that has lost some functionality. Additionally, each patient's natural gait may differ from another patient's gait, each requiring a different response from the orthosis during movement. Finally, as a patient has their functionality improve or worsen, the patient may need to adjust the orthosis to maintain their natural gait.

BRIEF SUMMARY

This disclosure generally relates to orthoses and methods to adjust and use said orthoses.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Description

Figure 1:
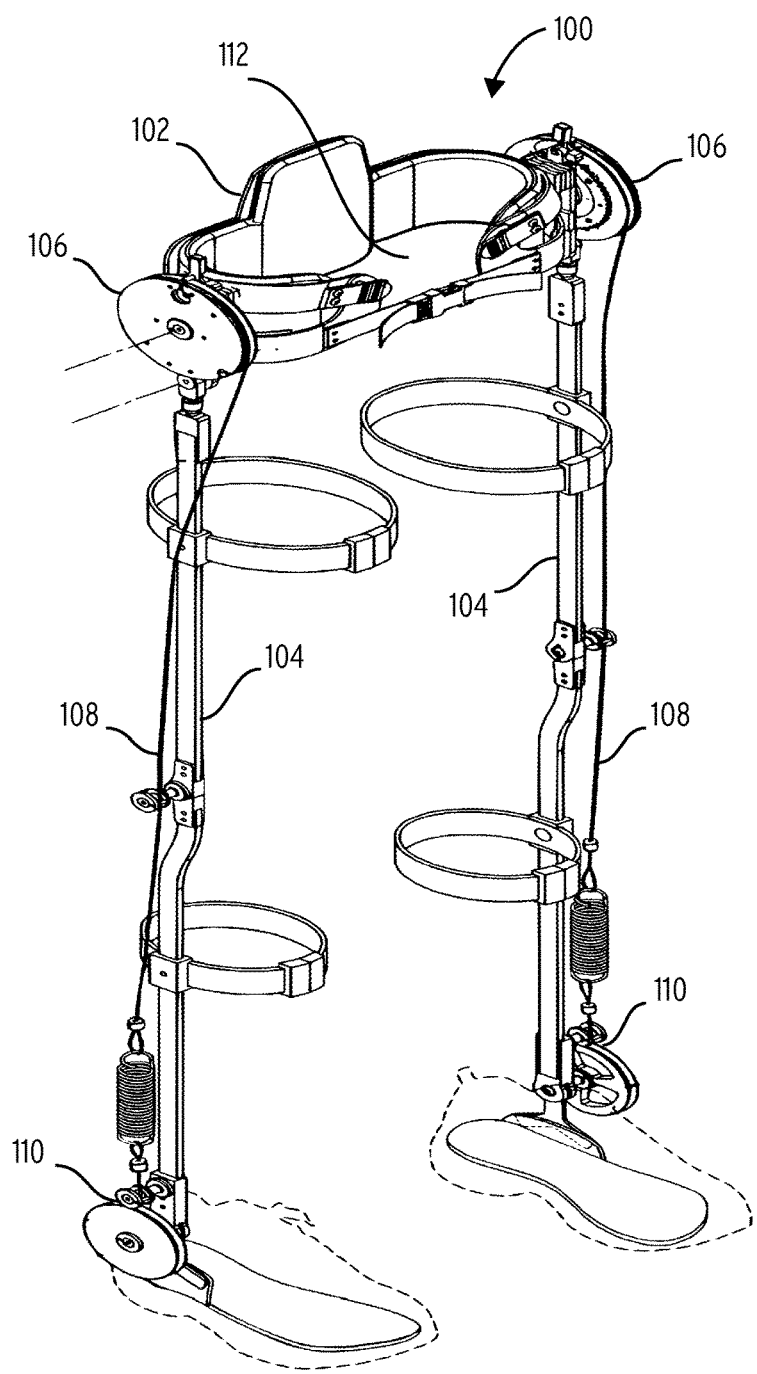
FIG. 1 illustrates an embodiment of a gate-assisting apparatus.

Embodiments of an apparatus are described that may assist a human gait. The components of the apparatus may be arranged to convert motion of the components relative to each other into stored potential energy. The arrangement of the components may then facilitate a gait as the potential energy is stored and released. The apparatus may be adjusted such that a more natural gait may be obtained.

In some embodiments, an apparatus for assisting a gait may include a harness and at least one brace that may include an articulated frame coupled to the harness, a pre-tensioning device, an energy-transforming mechanism, and/or the lower assembly coupled to the articulated frame. The harness may circumferentially secure a first enclosed region.

In some embodiments, the articulated frame coupled to the harness may include an upper component and a lower component. The apparatus may further include a force-directing device fixed to the articulated frame with a channel tangentially aligned with an energy-transforming mechanism. One or more force-directing devices may be coupled to the upper component and/or lower component. Additionally, the articulated frame may further include a leg harness coupled to the articulated frame, each leg harness may circumferentially secure or partially circumferentially secure an enclosed region.

In some embodiments, the pre-tensioning device may be coupled to the harness opposite of the first enclosed region may include at least one pawl, a pre-tensioning rim, and a centrally-located gear.

In some embodiments, the energy-transforming mechanism may include an energy storage device coupled to the pre-tensioning device via a superior exotendon and coupled to a lower assembly via an inferior exotendon. The energy-transforming mechanism may traverse a lower wheel groove to attach to a lower wheel attachment. The energy-transforming mechanism may be rotatably guided around the pre-tensioning device, rotatably guided around the force-directing device, rotatably guided around the tensioner, and counter-rotatably guided around the lower wheel. In embodiments with a plurality of force-directing devices, the energy-transforming mechanism may be either rotatably- or counter-rotatably guided around each force-directing device. In some embodiments, the energy storage device may be elastically positioned between the force-directing device(s) and the ankle-attaching mechanism. In yet further embodiments, the energy storage device may be a coil spring, which may provide a ratio of a maximum tension to a minimum tension of about 3 to about 20 and may have a tension range of about 3 lbf to about 40 lbf.

In some embodiments, the lower assembly may further include a tensioner, a lower wheel, and a foot plate that may be coupled to the inferior exotendon. The lower wheel may further include a lower wheel attachment, which may be located internal to the lower wheel, and a lower wheel groove. In some embodiments, the lower wheel may have a lower wheel tensioner groove. The tensioner may be fixed in a position such that it traverses the lower wheel tensioner groove.

The lower wheel tensioner groove may have a lower wheel tensioner groove transition, which may be tapered. In some embodiments, the tensioner may further include a tensioner exotendon groove that the energy-transforming mechanism may traverse.

In some embodiments, a method may include flexing a first joint assembly in response to receiving an impulse on an articulated frame, engendering movement of an energy-transforming mechanism coupled to the lower component via a lower assembly in response to flexing the first joint assembly, tensioning the energy-transforming mechanism to store a potential energy in an energy storage device in response to engendered movement of the energy-transforming mechanism, releasing the potential energy in the energy storage device in response to termination of the impulse, and/or extending the first joint assembly in response to releasing the potential energy in the energy storage device. In some embodiments, the first joint assembly may include a lower component that may move relative to an upper component. In further embodiments, such a method may further include regulating tension of the energy-transforming mechanism in response to articulation of a foot plate.

In some embodiments, a method may include tensioning an energy-transforming mechanism in response to an impulse, storing a potential energy in an energy storage device in response to tensioning the energy-transforming mechanism, and/or engaging a potential energy-maintaining device in response to termination of the impulse. Such a method may further include rotating a pre-tensioning rim of a pre-tensioning device in response to the impulse and/or tensioning the energy-transforming mechanism in response to rotating the pre-tensioning rim. In further embodiments, such a method may include counter-rotating a pre-tensioning rim in response to termination of the impulse, counter-rotating a centrally-located gear in response to counter-rotating the pre-tensioning rim, and/or engaging the potential energy-maintaining device with the centrally-located gear in response to counter-rotating the centrally-located gear. In some embodiments, the potential energy-maintaining device may be at least one pawl.

Drawings

FIG. 1 illustrates an embodiment of a gate-assisting apparatus 100. The gate-assisting apparatus 100 may comprise harness 102, articulated frame 104, pre-tensioning device 106, energy-transforming mechanism 108, lower assembly 110, and first enclosed region 112.

Harness 102 may secure a first enclosed region 112. Harness 102 may have devices for securing to itself to enclose the first enclosed region 112. Harness 102 may also have adjustment device to ensure a secure fit to a user. Harness 102 may have coupling devices to attach one or more brace.

Harness 102 may be coupled to at least one brace. In FIG. 1, harness 102 is shown coupled to two braces. Gate-assisting apparatus 100 may be configured to have only one brace coupled to harness 102 in some embodiments. Such embodiments may benefit users only needing gait assistance for one leg. Some embodiments may comprise more than two braces.

Each brace may comprise articulated frame 104, pre-tensioning device 106, energy-transforming mechanism 108, and lower assembly 110.

Articulated frame 104 may be coupled to pre-tensioning device 106 and lower assembly 110. Articulated frame 104 may also further comprise an upper component and a lower component. The upper component and lower component may be coupled by a knee joint. Articulated frame 104 may couple to pre-tensioning device 106 to allow motion in one or more planes. In some embodiments, the coupling may be by a hinge allowing for rotation in one plane. In another embodiment, the coupling may be by a dual-axis joint, wherein the planes may be orthogonal. In yet other embodiments, the coupling may be by a ball joint.

Articulated frame 104 may further comprise at least one leg harness. Each leg harness may be coupled to the upper component or the lower component. In some embodiments, each leg harness may secure a separate enclosed region. The user may secure their leg with each leg harness enabling better transfer of motion of their leg to the gate-assisting apparatus 100 and vice versa. In FIG. 1, each brace is shown with two leg harnesses. In other embodiments, each leg harness may partially enclose a region.

Pre-tensioning device 106 may be coupled to harness 102, articulated frame 104, and energy-transforming mechanism 108. Pre-tensioning device 106 may further comprise a pre-tensioning rim, a centrally-located gear, and at least one pawl. In some embodiments, the centrally-located gear and the at least one pawl may engage. In some embodiments, this engagement may allow rotation of the centrally-located gear relative to the at least one pawl in one direction. In yet another embodiment, the at least one pawl may be re-positioned relative to the centrally-located gear to disengage the at least one pawl from the centrally-located gear.

Energy-transforming mechanism 108 is coupled to pre-tensioning device 106 and lower assembly 110. Energy-transforming mechanism 108 may further comprise a superior exotendon, an inferior exotendon, and an energy storage device. Tension may be placed upon energy-transforming mechanism 108 either by the pre-tensioning device 106 or the motion of articulated frame 104 being transferred through lower assembly 110. Energy-transforming mechanism 108 may store potential energy in the energy storage device. In some embodiments, the energy storage device is a coil spring that elongates under tension, thereby storing potential energy.

Lower assembly 110 is coupled to the articulated frame 104 and the energy-transforming mechanism 108. Lower assembly 110 may comprise a lower wheel, a tensioner, and a foot plate. The lower wheel is coupled to energy-transforming mechanism 108, while the tensioner guides energy-transforming mechanism 108.

Figure 2:
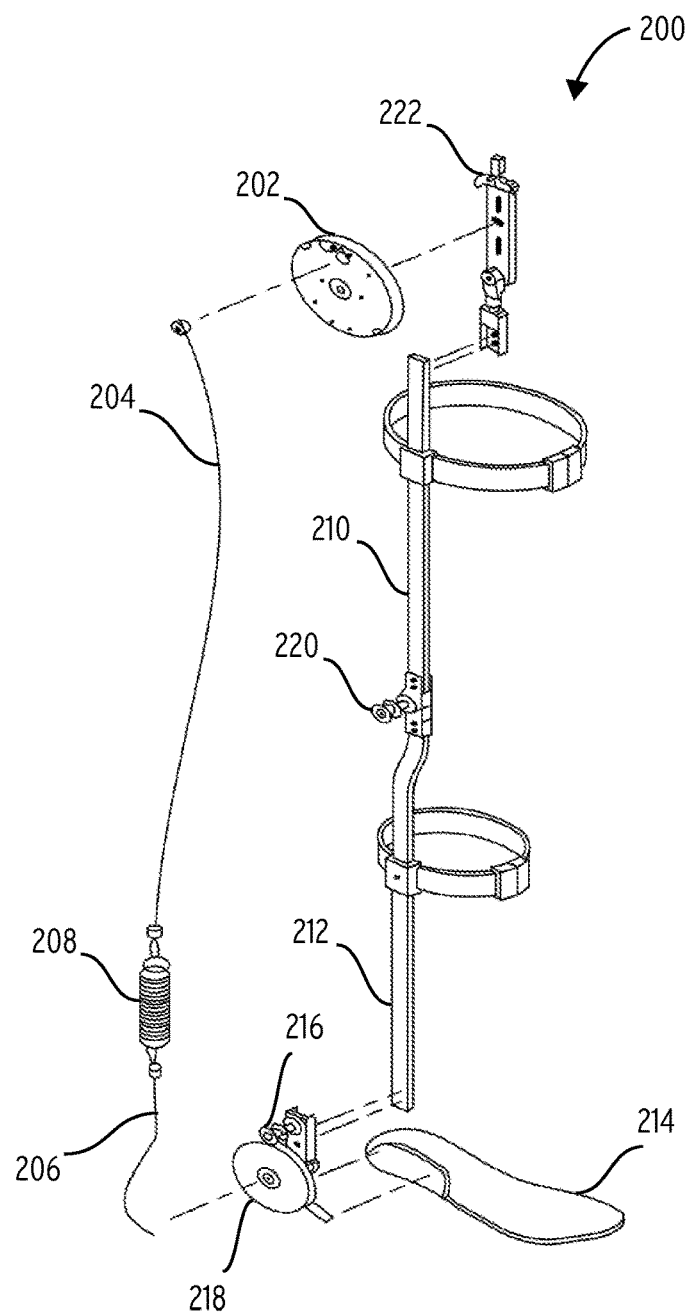
FIG. 2 illustrates an embodiment of a brace in an exploded view.

FIG. 2 illustrates an embodiment of a brace 200 in an exploded view. The brace 200 may comprise pre-tensioning rim 202, superior exotendon 204, inferior exotendon 206, energy storage device 208, upper component 210, lower component 212, foot plate 214, tensioner 216, lower wheel 218, force-directing device 220, and pawl 222.

Pre-tensioning rim 202 may be coupled to superior exotendon 204 and harness 102. Additionally, pre-tensioning rim 202 may engage with pawl 222. In some embodiments pre-tensioning rim 202 may be approximately cylindrical. In some embodiments, superior exotendon 204 may be coupled proximate to the circumference of pre-tensioning rim 202. Superior exotendon 204 may then engage with the circumference of pre-tensioning rim 202 as pre-tensioning rim 202 is rotated. In some embodiments, pre-tensioning rim 202 may have a groove or channel along its circumference in which superior exotendon 204 may engage when pre-tensioning rim 202 is rotated.

In some embodiments, pre-tensioning rim 202 may have a feature that may extend approximately perpendicular to the circumference of pre-tensioning rim 202. Such a device may be rotatably attached to pre-tensioning rim 202 and may reside internal to pre-tensioning rim 202 upon rotation.

Superior exotendon 204 may be further coupled to energy storage device 208. In some embodiments, superior exotendon 204 may traverse force-directing device 220. In other embodiments, superior exotendon 204 may traverse a plurality of force-directing device 220. The length of superior exotendon 204 may be altered to position energy storage device 208 relative to pre-tensioning rim 202.

Inferior exotendon 206 may be coupled to energy storage device 208 and lower wheel 218. In some embodiments, inferior exotendon 206 may traverse force-directing device 220. In other embodiments, inferior exotendon 206 may traverse a plurality of force-directing device 220. The length of inferior exotendon 206 may be altered to position energy storage device 208 relative to pre-tensioning rim 202. In some embodiments, inferior exotendon 206 may traverse tensioner 216. In some embodiments, inferior exotendon 206 may traverse the circumference of lower wheel 218.

Energy storage device 208 may be coupled to superior exotendon 204 and inferior exotendon 206. Energy storage device 208 may be any device that may store potential energy. In some embodiments in which superior exotendon 204 traverses force-directing device 220, energy storage device 208 may reside between the traverse of superior exotendon 204 around force-directing device 220 and the traverse of inferior exotendon 206 around tensioner 216. In some embodiments, energy storage device 208 may be a coil spring. In further embodiments, the coil spring may have a ratio of a maximum tension to a minimum tension of about 3 to about 20. The coil spring may also have a tension range of about 3 lbf to about 40 lbf.

Upper component 210 may be coupled to pre-tensioning rim 202, pawl 222, and lower component 212. In some embodiments, upper component 210 may be coupled to force-directing device 220. In other embodiments, upper component 210 may be coupled to a plurality of force-directing device 220. Upper component 210 may be coupled to lower component 212 by a joint. In some embodiments, the joint may allow rotation of upper component 210 relative to lower component 212 in one plane. In other embodiments, upper component 210 may rotate in more than one plane relative to lower component 212. In some embodiments, upper component 210 may be coupled to one or more harnesses that enclose or partially enclose a region.

Lower component 212 may be further coupled to foot plate 214, tensioner 216, and lower wheel 218. In other embodiments, lower component 212 may be coupled to a plurality of force-directing device 220. In some embodiments, lower component 212 may be coupled to one or more harnesses that enclose or partially enclose a region. Lower component 212 may be coupled to foot plate 214 by a joint. In some embodiments, the joint may allow rotation of lower component 212 relative to foot plate 214 in one plane. In other embodiments, lower component 212 may rotate in more than one plane relative to foot plate 214. Lower component 212 may be coupled to tensioner 216 and lower wheel 218 such that tensioner 216 and lower wheel 218 may rotate independent of lower component 212.

Foot plate 214 may be further coupled to tensioner 216 and lower wheel 218. In some embodiments, foot plate 214 may rotate independent of tensioner 216 and lower wheel 218. In other embodiments, foot plate 214 may be coupled to lower wheel 218 such that rotation of either will induce rotation of the other. In some embodiments, foot plate 214 may be oriented to engage a surface with its side with the largest surface area. In some embodiments, foot plate 214 may approximate the shape of a sole of a foot.

Tensioner 216 may be further coupled to lower wheel 218. In some embodiments, lower wheel 218 may rotate independent of tensioner 216. In some embodiments, tensioner 216 may engage inferior exotendon 206. In yet other embodiments, tensioner 216 may have a channel by which it engages inferior exotendon 206. In some embodiments, tensioner 216 may rotate independent of lower component 212, foot plate 214, and lower wheel 218.

Lower wheel 218 may be approximately cylindrical. In some embodiments, lower wheel 218 may have an internal lower wheel attachment to couple with inferior exotendon 206. Lower wheel 218 may also have a lower wheel groove about its circumference that inferior exotendon 206 may traverse. In some embodiments, lower wheel 218 may have a groove in its circumference. In some embodiments, tensioner 216 may traverse the groove. The groove in the circumference of lower wheel 218 may be tapered.

Force-directing device 220 may be coupled to upper component 210 or lower component 212. In some embodiments, force-directing device 220 may be coupled to a knee joint that couples upper component 210 to lower component 212. In some embodiments, a plurality of force-directing device 220 may be coupled to upper component 210 and lower component 212. In some embodiments, force-directing device 220 may be adjustably coupled to upper component 210 or lower component 212. In some embodiments, force-directing device 220 may have a force-directing channel upon which superior exotendon 204 or inferior exotendon 206 may traverse.

Pawl 222 may engage with a centrally-located gear coupled to pre-tensioning rim 202. In some embodiments, pawl 222 may disengage with the centrally-located gear. In further embodiments, a spring may be used to enable engagement with the centrally-located gear.

Figure 3:
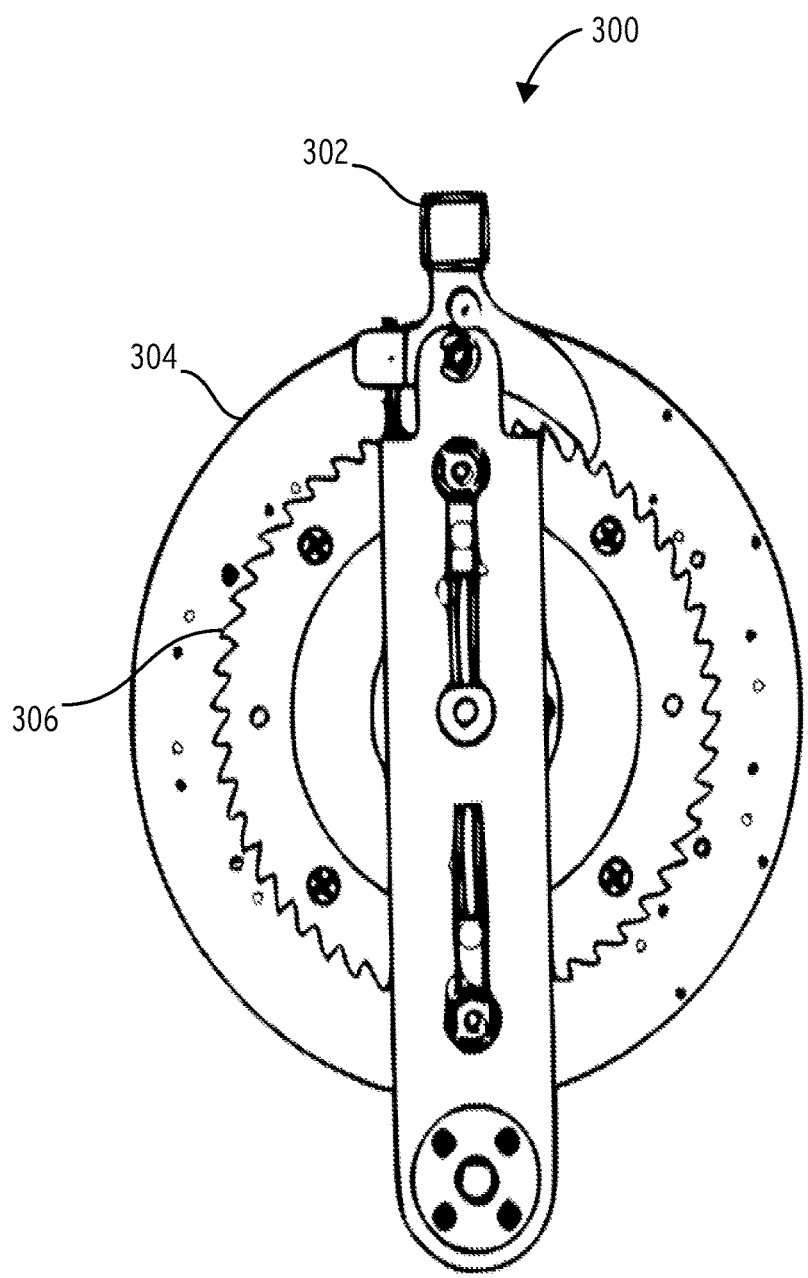
FIG. 3 illustrates an embodiment of a pre-tensioning device.

FIG. 3 illustrates an embodiment of a pre-tensioning device 300. Pre-tensioning device 300 may comprise pawl 302, pre-tensioning rim 304, and centrally-located gear 306.

Pawl 302 may be coupled to pre-tensioning rim 304 and centrally-located gear 306. In some embodiments, pre-tensioning rim 304 and centrally-located gear 306 may rotate independent of pawl 302. Pawl 302 may also engage centrally-located gear 306, enabling rotation in only one direction while engaged. In some embodiments, pawl 302 may have a pivot by which it may become disengaged with centrally-located gear 306. In some embodiments, pawl 302 may have a spring that may induce engagement.

Pre-tensioning rim 304 may be further coupled to centrally-located gear 306. In some embodiments, rotation of pre-tensioning rim 304 may induce rotation of centrally-located gear 306. In some embodiments, pre-tensioning rim 304 may have a feature that extends approximately perpendicular to the circumference of pre-tensioning rim 304. Such a device may be rotatably attached to pre-tensioning rim 304 and may reside internal to pre-tensioning rim 304 upon rotation.

Centrally-located gear 306 may have one or more engagement feature by which to engage pawl 302. In some embodiments, the engagement features are gear teeth that may engage pawl 302 when pre-tensioning rim 304 rotates in one direction (in FIG. 3, counter clockwise) while not engaging when pre-tensioning rim 304 rotates in the opposite direction (in FIG. 3, clockwise).

Figure 4:
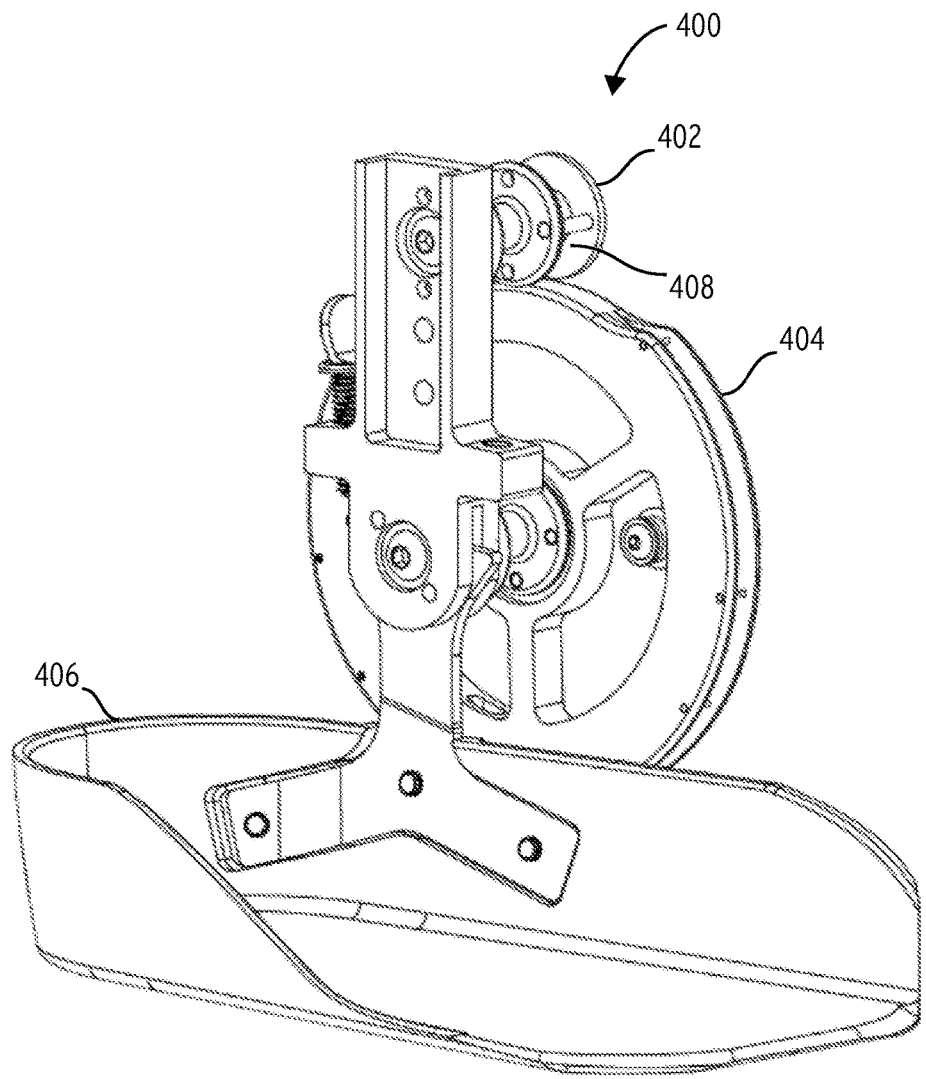
FIG. 4 illustrates an embodiment of a lower assembly.

FIG. 4 illustrates an embodiment of a lower assembly 400. Lower assembly 400 may comprise tensioner 402, lower wheel 404, foot plate 406, and tensioner exotendon groove 408.

Tensioner 402 may be coupled to lower wheel 404 and foot plate 406. In some embodiments, tensioner 402 may have a tensioner exotendon groove 408 in which an exotendon may traverse. Tensioner 402 may rotate about a central axis in an approximately circular manner. In some embodiments, tensioner 402 may be approximately cylindrical.

Lower wheel 404 may further be coupled to foot plate 406. In some embodiments, lower wheel 404 may rotate when foot plate 406 is rotated. In other embodiments, lower wheel 404 rotates independently of foot plate 406.

Figure 5:
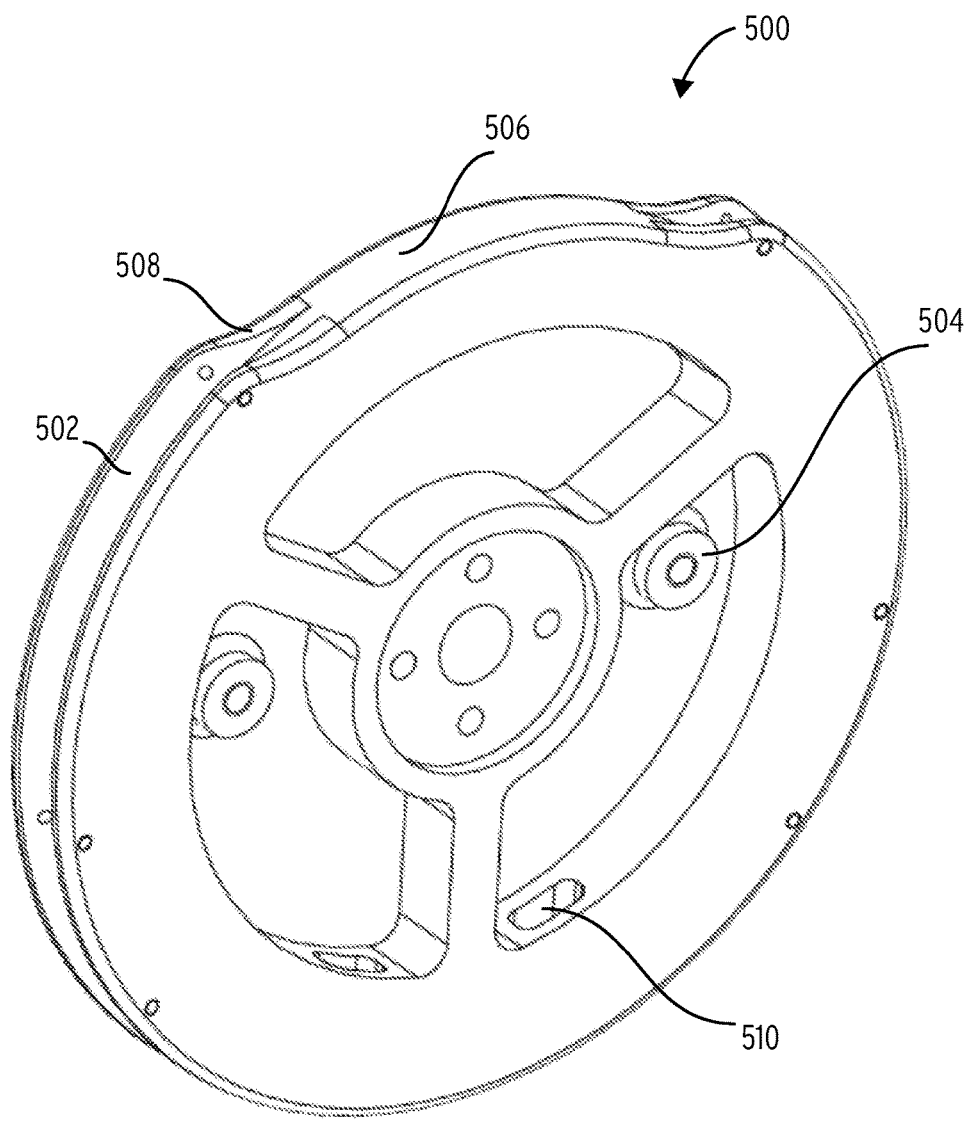
FIG. 5 illustrates an embodiment of a lower wheel.
Figure 6:
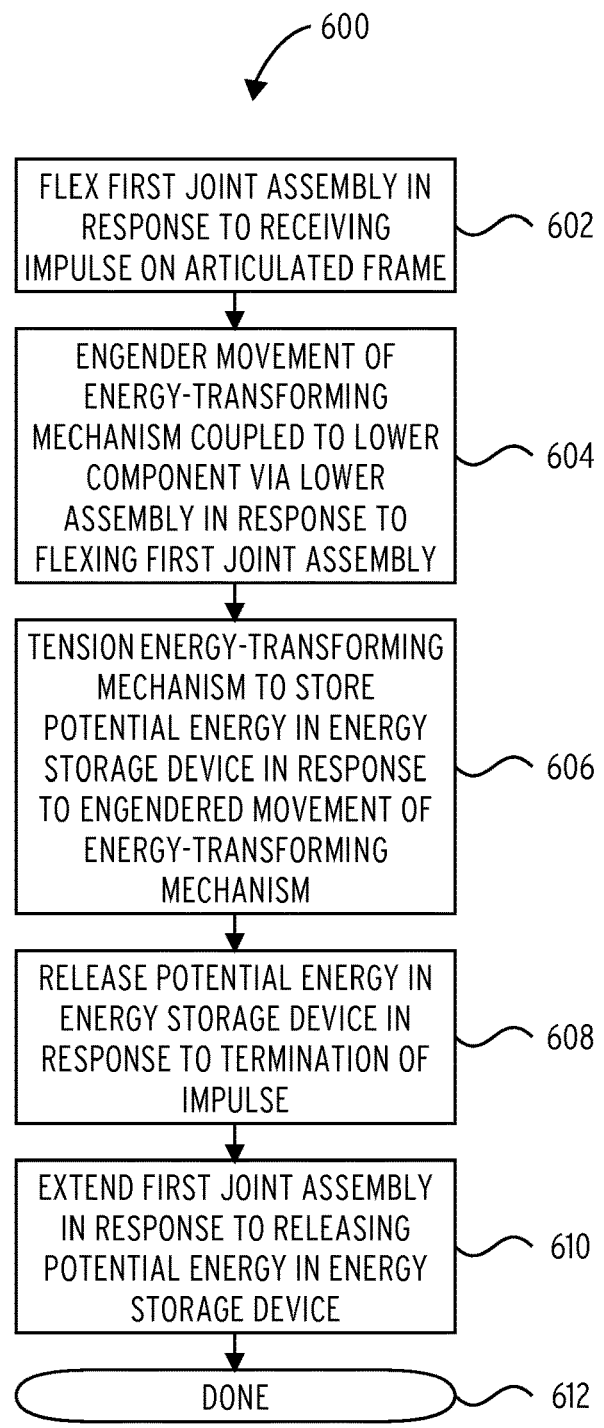
FIG. 6 illustrates an embodiment of a gait assisting method.
Figure 7:
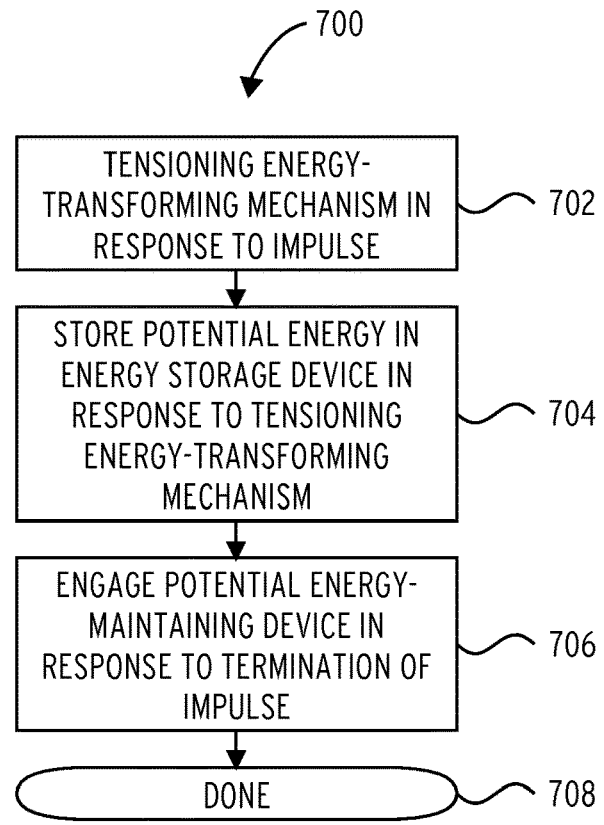
FIG. 7 illustrates an embodiment of a pre-tensioning method.

FIG. 5 illustrates an embodiment of a lower wheel 500. Lower wheel 500 may comprise lower wheel groove 502, lower wheel attachment 504, tensioner wheel groove 506, tensioner wheel groove transition 508, and exotendon hole 510.

Lower wheel groove 502 may be present along the circumference of lower wheel 500. Lower wheel groove 502 may completely or partially circumnavigate lower wheel 500. The inferior exotendon may traverse lower wheel groove 502.

Lower wheel attachment 504 may be coupled to lower wheel 500. In some embodiments, lower wheel 500 may have a plurality of lower wheel attachment 504. An inferior exotendon may couple to lower wheel 500 at lower wheel attachment 504.

Tensioner wheel groove 506 may be present upon the outer circumference of lower wheel 500. Tensioner wheel groove 506 may have a tensioner wheel groove transition 508. In some embodiments, the tensioner wheel groove transition 508 may be tapered. In some embodiments, lower wheel 500 may be oriented such that a tensioner may traverse the tensioner wheel groove 506.

Exotendon hole 510 may be located between an outer circumference of lower wheel 500 and an inner circumference of lower wheel 500. An inferior exotendon may traverse exotendon hole 510 to couple with tensioner wheel groove transition 508. In some embodiments, lower wheel 500 may have a plurality of exotendon hole 510.

In block 602, gait assisting method 600 flexes a first joint assembly in response to receiving an impulse on an articulated frame.

In block 604, gait assisting method 600 engenders movement of an energy-transforming mechanism coupled to the lower component via a lower assembly in response to flexing the first joint assembly.

In block 606, gait assisting method 600 tension the energy-transforming mechanism to store a potential energy in an energy storage device in response to engendered movement of the energy-transforming mechanism. In some embodiments, a foot plate may be articulated to further regulate the tension of the energy-transforming mechanism.

In block 608, gait assisting method 600 releases the potential energy in the energy storage device in response to termination of the impulse.

In block 610, gait assisting method 600 extends the first joint assembly in response to releasing the potential energy in the energy storage device.

In done block 612, gait assisting method 600 ends.

In block 702, pre-tensioning method 700 tensioning an energy-transforming mechanism in response to an impulse. In some embodiments tensioning of an energy-transforming mechanism may occur by rotating a pre-tensioning rim of a pre-tensioning device in response to the impulse, tensioning the energy-transforming mechanism in response to rotating the pre-tensioning rim.

In block 704, pre-tensioning method 700 stores a potential energy in an energy storage device in response to tensioning the energy-transforming mechanism.

In block 706, pre-tensioning method 700 engages a potential energy-maintaining device in response to termination of the impulse. In some embodiments, the potential energy-maintaining device may be engaged by counter-rotating a pre-tensioning rim in response to termination of the impulse, counter-rotating a centrally-located gear in response to counter-rotating the pre-tensioning rim; and engaging the potential energy-maintaining device with the centrally-located gear in response to counter-rotating the centrally-located gear. In further embodiments, the potential energy-maintaining device may be at least one pawl.

In done block 708, pre-tensioning method 700 ends.

What is claimed is:

1. An apparatus comprising:
   a harness, wherein the harness circumferentially secures a first enclosed region; and
   at least one brace comprising:
   an articulated frame articulably attached to the harness comprising an upper component, a lower component, and a force-directing device;
   the upper component articulably attached to the harness;
   the lower component formed to hingeably attach to the upper component at a knee joint;
   a pre-tensioning device, wherein the pre-tensioning device is coupled to the harness opposite of the first enclosed region, comprising at least one pawl, a pre-tensioning rim, and a centrally-located gear;
   an energy-transforming mechanism comprising an energy storage device coupled to the pre-tensioning device via a superior exotendon and coupled to a lower assembly via an inferior exotendon;
   the energy storage device elastically positioned between the force-directing device and the lower assembly; and
   the lower assembly coupled to the articulated frame, wherein the lower assembly further comprises a tensioner, a lower wheel coupled to the inferior exotendon, and a foot plate hingeably attached to the lower wheel.

2. The apparatus of claim 1 wherein the energy storage device is a coil spring.

3. The apparatus of claim 2 wherein the coil spring has a ratio of a maximum tension to a minimum tension of about 3 to about 20.

4. The apparatus of claim 2 wherein the coil spring has a tension range of about 3 lbf to about 40 lbf.

5. The apparatus of claim 1 wherein the lower wheel further comprises a lower wheel tensioner groove and a lower wheel tensioner groove transition, and the tensioner is positioned proximate to the lower wheel tensioner groove transition.

6. The apparatus of claim 5 wherein the lower wheel tensioner groove transition is tapered.

7. The apparatus of claim 1 wherein the force-directing device is coupled to the knee joint.

8. The apparatus of claim 1 wherein the lower wheel further comprises a lower wheel attachment and a lower wheel groove, wherein the inferior exotendon traverses the lower wheel groove to attach to the lower wheel attachment.

9. The apparatus of claim 1 wherein the tensioner further comprises a tensioner exotendon groove, wherein the energy-transforming mechanism traverses the tensioner exotendon groove.

10. The apparatus of claim 1 wherein the force-directing device further comprises a force-directing channel tangentially aligned with the energy-transforming mechanism.

11. The apparatus of claim 1 wherein the energy-transforming mechanism is rotatably guided around the pre-tensioning device, rotatably guided around the force-directing device, rotatably guided around the tensioner, and counter-rotatably guided around the lower wheel.

12. The apparatus of claim 1 further comprising at least one leg harness coupled to the articulated frame, wherein each of the at least one leg harness circumferentially secures a second enclosed region.

* * * * *